US007297140B2

(12) United States Patent
Orlu et al.

(10) Patent No.: US 7,297,140 B2
(45) Date of Patent: Nov. 20, 2007

(54) PERFORATING CONNECTOR WITH STERILE CONNECTION

(75) Inventors: Alain Orlu, Viuz la Chiesaz (FR); Pierre-André Commaret, Bogis-Bossey (CH)

(73) Assignee: P2A Medical, Albens (FR)

( * ) Notice: Subject to any disclaimer, the term of this patent is extended or adjusted under 35 U.S.C. 154(b) by 335 days.

(21) Appl. No.: 11/068,236

(22) Filed: Feb. 28, 2005

(65) Prior Publication Data

US 2005/0203481 A1 Sep. 15, 2005

(30) Foreign Application Priority Data

Mar. 10, 2004 (FR) .................................. 04 02568

(51) Int. Cl.
*A61B 19/00* (2006.01)
*B65D 41/62* (2006.01)

(52) U.S. Cl. ...................... 604/411; 604/412; 604/413; 604/414; 215/277

(58) Field of Classification Search ........ 604/411–415, 604/403; 215/254, 272, 277
See application file for complete search history.

(56) References Cited

U.S. PATENT DOCUMENTS 5,445,631 A * 8/1995 Uchida ....................... 604/412
5,478,337 A * 12/1995 Okamoto et al. ........... 604/413
5,879,345 A * 3/1999 Aneas ........................ 604/411
6,159,192 A * 12/2000 Fowles et al. .............. 604/403
2003/0199846 A1 10/2003 Fowles

FOREIGN PATENT DOCUMENTS

WO WO-03082398 A2 10/2003

* cited by examiner

*Primary Examiner*—Tatyana Zalukaeva
*Assistant Examiner*—Phil Wiest
(74) *Attorney, Agent, or Firm*—William H. Eilberg

(57) ABSTRACT

A connector according to the invention comprises a hollow needle fastened to a body. A first tubular receptacle provided with a first foil surrounds a first end section of the needle. A second tubular receptacle provided with a second foil surrounds a second end section of the needle. The tubular receptacles are able to slide on the body. The holding sleeve moves the body toward the first foil over a first piercing stroke to pierce it, and then moves the second foil toward the body over a second piercing stroke to pierce it. In this way there may be obtained simultaneous piercing of the foils and foils or stoppers of containers such as flasks or sachets pressed against the foils, to provide a connection under optimum conditions of sterility.

12 Claims, 4 Drawing Sheets

PERFORATING CONNECTOR WITH STERILE CONNECTION

TECHNICAL FIELD OF THE INVENTION

The present invention concerns perforating connectors for connecting a first container and a second container together in order to pass a fluid between the two containers. The containers may be tubes, flasks, flexible wall sachets, having a mouth blocked by a foil through which a hollow needle can pass.

The invention concerns more specifically a connector of the above kind provided with a hollow fluid passage needle adapted to pierce a first foil of the first container and a second foil of the second container in order to pass fluid through the axial passage of the needle between the two containers.

Perforating connectors of the above kind have already been designed comprising a hollow fluid passage needle and a needle support body fixed in a sealed manner around an intermediate section of the needle to leave projecting first and second end portions of the needle adapted to pass through the foils of the containers.

The ends of the needle are sharp and constitute a hazard for personnel manipulating the connector. Perforating connectors of the above kind further necessitate protection of the needle against contamination to ensure sterility before use. To this end, the documents WO 03/082398 A and U.S. 2003/0199846 A1 describe a connector further comprising a first tubular receptacle surrounding the first end section of the needle, closed by a first foil, and conformed to receive a first container to be connected, and a second tubular receptacle surrounding the second end section of the needle, closed by a second foil, and conformed to receive a second container to be connected. The foils can slide axially toward each other and the needle is mounted on an interior body that slides freely relative to both foils. On moving the foils toward each other, they are pierced by respective ends of the needle.

The needle is therefore confined in a sealed enclosure that protects it from all risks of pollution until the moment at which the needle simultaneously pierces the wall of the sealed enclosure and the foils of the containers to be connected. It is therefore possible, in practice, to disinfect locally, before piercing, the external surfaces of the sealed enclosure wall and the foils of the containers that will be pierced by the needle, thus minimizing the risks of polluting particles being entrained during piercing.

The above kind of perforating connector structure necessitates placing the two containers to be connected simultaneously on respective opposite sides of the foils. Failing this, there is a risk of the needle, which is not retained axially, perforating prematurely one of the foils that is not yet covered by a container, in which case sterility would no longer be assured, and the user might be injured.

SUMMARY OF THE INVENTION

The problem addressed by the invention is that of preventing, in the above kind of perforating connector, all risks of premature piercing of the sealed enclosure wall before placing the containers; premature piercing would not only cause pollution of the needle but also lead to a high risk of injury to the personnel using the connector.

It is necessary in particular to prevent any risk of the needle piercing the sealed enclosure in the absence of a container to be connected.

The invention also seeks to facilitate manipulation of the perforating connector, in particular to effect piercing by means of simple movements in axial translation.

To achieve the above and other objects, the invention starts from the general structure of a perforating connector, comprising a hollow fluid passage needle, a needle support body fixed in a sealed manner around an intermediate section of the needle and allowing a first end section and a second end section of the needle to project, a first tubular receptacle around the first end section of the needle and conformed to receive a first element to be connected, a second tubular receptacle around the second end section of the needle and conformed to receive a second element to be connected, a first foil closing the first tubular receptacle, a second foil closing the second tubular receptacle, the first foil being movable axially relative to the needle support body over a first piercing stroke between an initial position away from the body and the needle and a final position close to the body in which the needle passes through the first foil and its end projects toward the exterior of the connector, this second foil being movable axially relative to the needle support body over a second piercing stroke between an initial position away from the body and the needle and a final position close to the body in which the needle passes through the second foil and its end projects toward the exterior of the connector.

According to the invention, the perforating connector comprises a coaxial external holding sleeve adapted for moving the body axially and the second foil axially toward the first foil over the first piercing stroke and then to move the second foil axially toward the body and toward the first foil the second piercing stroke.

The user can therefore control the relative movements that lead to piercing of both the foils and can in particular be sure of preventing piercing of the second foil during piercing of the first foil, and can pierce the second foil only after ensuring that the second container to be connected is present.

In practice, in one advantageous embodiment of the invention, the holding sleeve is connected to the body and to the second foil by special mechanical connections enabling the above movements and entrainments. Thus:

- the sleeve comprises unilateral engagement means to enable the sleeve to push the body and the second foil axially toward the first foil when the sleeve moves axially over a distance equal to the first piercing stroke in the direction of the body, and for the sleeve to be disengaged axially from the body and the second foil when the sleeve effects a return stroke in the opposite direction away from the first foil and over a distance equal to the first piercing stroke,
- the sleeve comprises non-return engagement means in order for the sleeve to allow the second foil to be retained in a fixed position relative to the body during the return stroke in the opposite direction of the sleeve, and then for the sleeve to entrain the second foil from its initial position toward its final position when the sleeve effects a second piercing stroke in the direction of the first foil.

For example, the unilateral engagement means of the sleeve can comprise unilateral engagement means on the body, namely:

- a first larger diameter bore on a first end section of the sleeve delimited by a first shoulder and a second shoulder, and
- a larger diameter annular rib on the body, engaged in the first bore of the sleeve to allow relative axial movement of the sleeve around the body over an appropriate stroke equal to the first piercing stroke between two limiting positions in which the annular rib is abutted against one or the other of the shoulders.

Also, the unilateral engagement means of the sleeve can comprise unilateral engagement means on the second foil, namely:

a larger diameter second bore in a second end section of the sleeve delimited by a first shoulder and a second shoulder, and the second foil being engaged in the second bore to move over an appropriate axial stroke equal to the second piercing stroke.

For example, the non-return engagement means of the sleeve on the second foil may be such that the second bore comprises an annular intermediate rib having a sawtooth transverse profile with a non-inclined first face and an inclined second face and cooperating with the second foil to allow it to move in the direction of the first foil and to prevent any return movement thereof in the opposite direction.

To ensure easy and regular movement of the foils in the axial direction, means are preferably provided for guiding them. For example, the first foil is mounted on a first cylinder that slides in the sleeve and slides on the body with sealed sliding means between them. The first cylinder may constitute said first tubular receptacle.

For the same reasons, the second foil may be mounted on a second cylinder that slides in the sleeve and slides on the body with sealed sliding means between them. The second cylinder may constitute said second tubular receptacle.

It is preferable for the external faces of the two foils to remain accessible from the outside for disinfecting them prior to the piercing operations. To this end, in an initial position, the first cylinder advantageously projects out of the sleeve, and the second cylinder is engaged with the second foil in the vicinity of the second end of the sleeve.

BRIEF DESCRIPTION OF THE DRAWINGS

Other objects, features and advantages of the present invention will emerge from the following description of particular embodiments given with reference to the appended drawings, in which.

DESCRIPTION OF THE PREFERRED EMBODIMENTS

Figure 1:
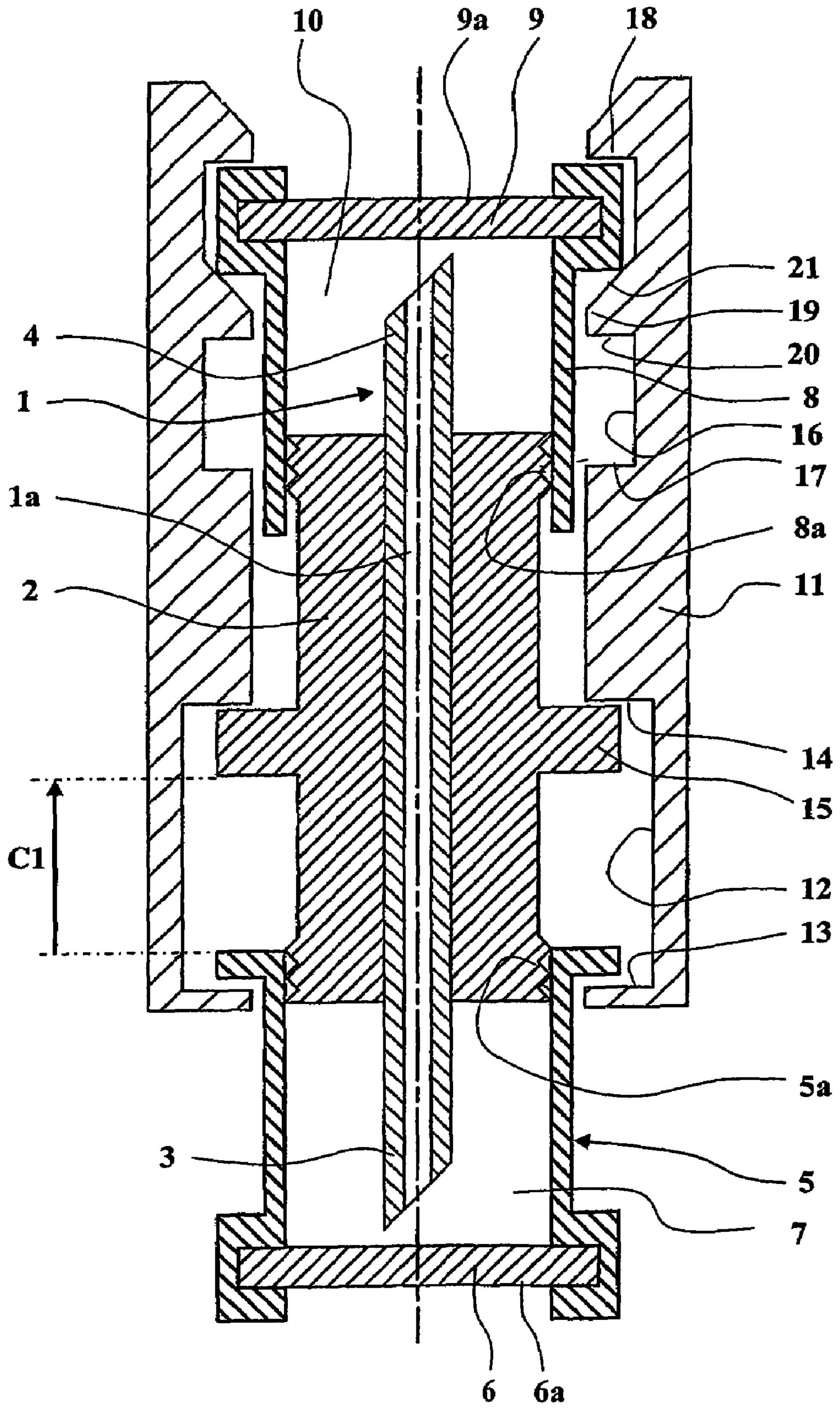
FIG. 1 is a side view in longitudinal section of one embodiment of a perforating connector of the present invention in an initial or transport position.

The embodiment of a perforating connector of the invention shown in the figures comprises a hollow needle 1 with an axial fluid passage 1*a*, and a needle support body 2 that surrounds and is fixed in a sealed manner to an intermediate section of the needle 1, and which leaves projecting a first end section 3 and a second end section 4 of the needle 1.

The first end section 3 of the needle 1 is surrounded by a first tubular receptacle 5 closed by a first foil 6. As a result, in an initial or transport position shown in FIG. 1, the first end section 3 of the needle 1 remains confined in a first cavity 7 delimited by the first foil 6, by the first tubular receptacle 5 and by the body 2.

Similarly, a second tubular receptacle 8 surrounds the second end section 4 of the needle 1 and is closed by a second foil 9. As a result, in an initial or transport position shown in FIG. 1, the second end section 4 of the needle 1 is confined in a second cavity 10 delimited by the second foil 9, by the second tubular receptacle 8 and by the body 2.

The first tubular receptacle 5 is conformed to be coupled to a first container to be connected, for example on being pressed axially against a foil or stopper of a first flask.

Similarly, the second tubular receptacle 8 is conformed to be coupled to a second container to be connected, for example by being pressed axially against a second foil or stopper of a second flask.

Figure 2:
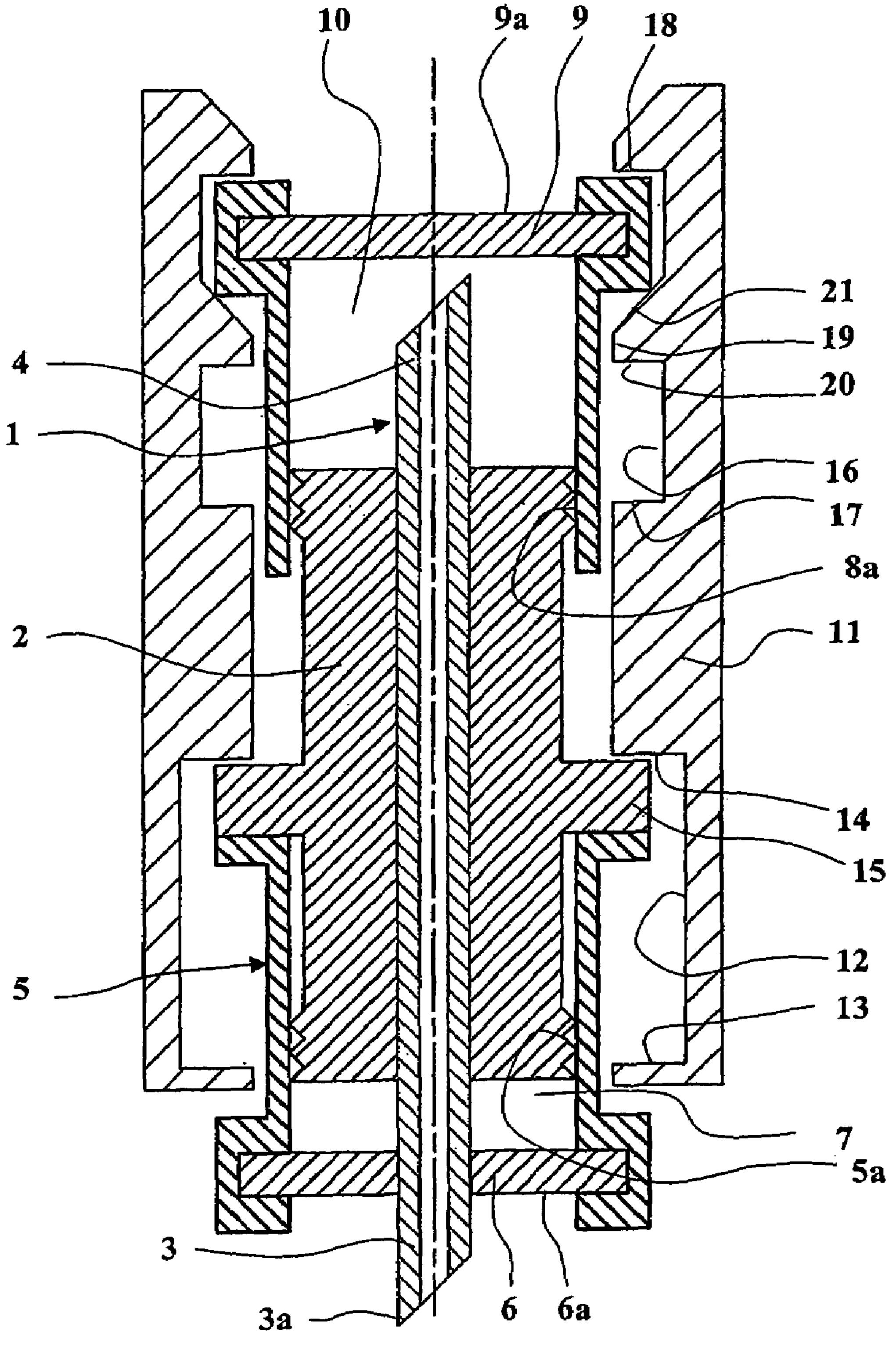
FIG. 2 is a side view in section of the FIG. 1 connector after a first perforation stroke has led to perforation of the first foil.

The combination of the first foil 6 and the first tubular receptacle 5 is able to slide on the body 2, so that the first foil 6 is movable axially relative to the needle support body 2 over a first piercing stroke C1: the first piercing stroke C1 is defined as the movement in axial translation of the first foil 6 from an initial position, shown in FIG. 1, in which the first foil 6 is away from the body 2 and the needle 1, to a final position, shown in FIG. 2, in which the first foil 6 has been moved toward the body 2, the needle 1 has passed through the first foil 6, and its end 3*a* projects toward the exterior of the connector.

Figure 3:
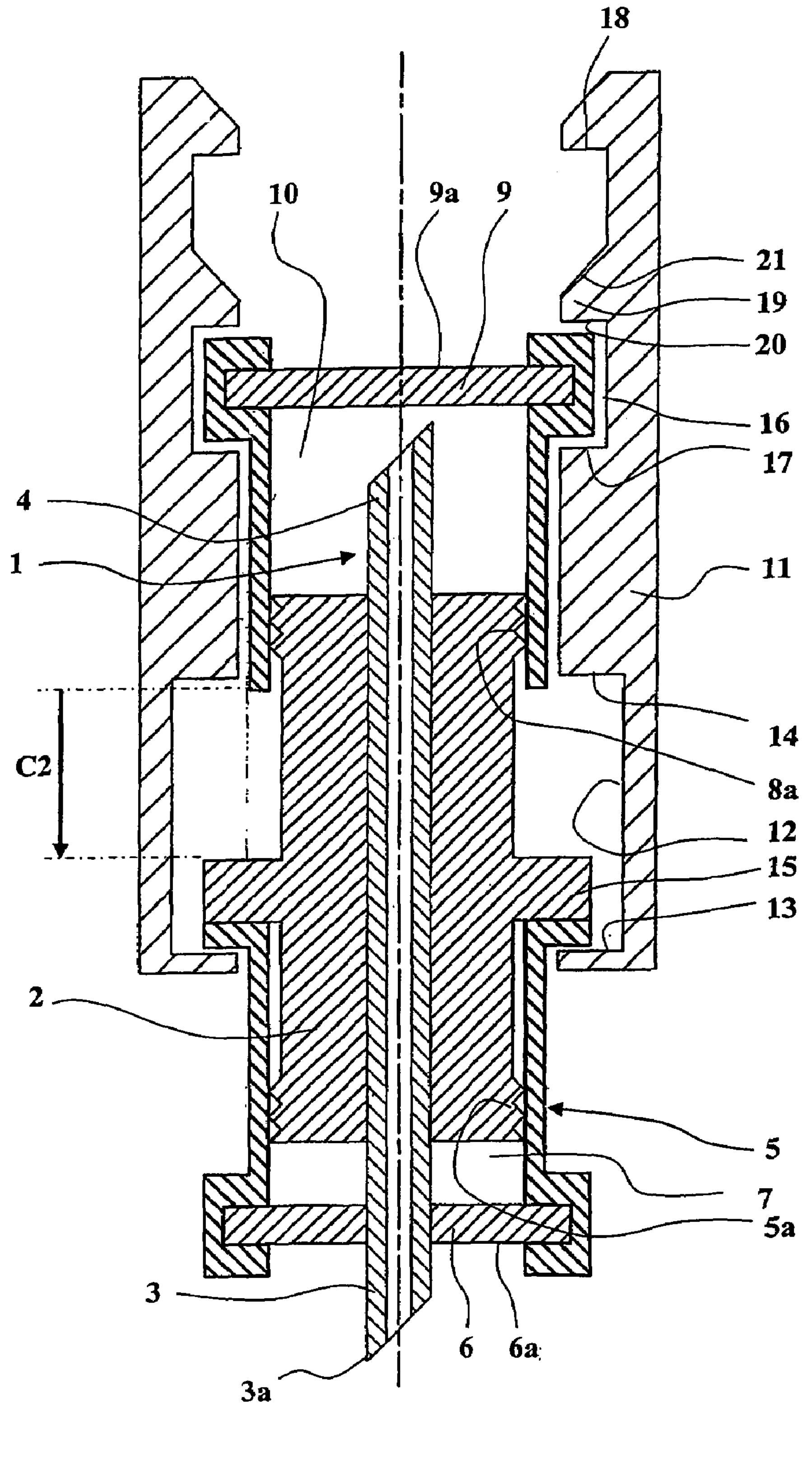
FIG. 3 is a side view in section of the FIG. 1 connector after a return stroke in the opposite direction.

Similarly, the combination of the second foil 9 and the second tubular receptacle 8 is able to slide on the body 2, so that the second foil 9 is movable axially relative to the needle support body 2 over a second piercing stroke C2 (FIG. 3). The second piercing stroke C2 is defined as the movement in axial translation of the second foil 9 from an initial position, shown in FIGS. 1 to 3, in which the second foil 9 is away from the body 2 and the needle 1, to a final position, shown in FIG. 4, in which the second foil 9 has been moved toward the body 2, the needle 1 has passed through the second foil 9, and its end 4*a* projects toward the exterior of the connector.

The two foils 6 and 9 are movable independently of each other toward and away from the body 2.

Thus the first foil 6 is mounted on a first tubular receptacle 5 in the form of a first cylinder that slides on the body 2 with first sealed sliding means 5*a* between them, for example a plurality of annular ribs on the body 2.

Similarly, the second foil 9 is mounted on a second tubular receptacle 8 in the form of a cylinder that slides on the body 2 with sealed sliding means 8*a* between them, for example a plurality of annular ribs on the body 2.

An external coaxial sleeve 11 is provided to constitute holding means for axially moving the body 2 toward the first foil 6 over a distance equal to the first piercing stroke C1, entraining the second foil 9, and then moving the second foil 9 axially toward the body 2 and toward the first foil 6 over the second piercing stroke C2.

To this end, the sleeve 11 comprises unilateral engagement means for pushing the body 2 axially toward the first foil 6, so that the sleeve 11 effects the first piercing stroke in the direction of the body 2, i.e. the stroke illustrated from FIG. 1 to FIG. 2. During this first piercing stroke, the first foil 6 bears axially against a first container, so that it is subjected to a relative movement toward the body 2 over said first piercing travel.

The unilateral engagement means then allow the sleeve 11 to effect a return stroke in the opposite direction to the first piercing stroke, away from the first foil 6, i.e. to move from the FIG. 2 position to the FIG. 3 position. During this return stroke, the second foil 9 bears axially against a second container, and non-return engagement means on the sleeve 11 hold the second foil 9 fixed in position relative to the body 2, allowing it to slide in the sleeve 11.

Figure 4:
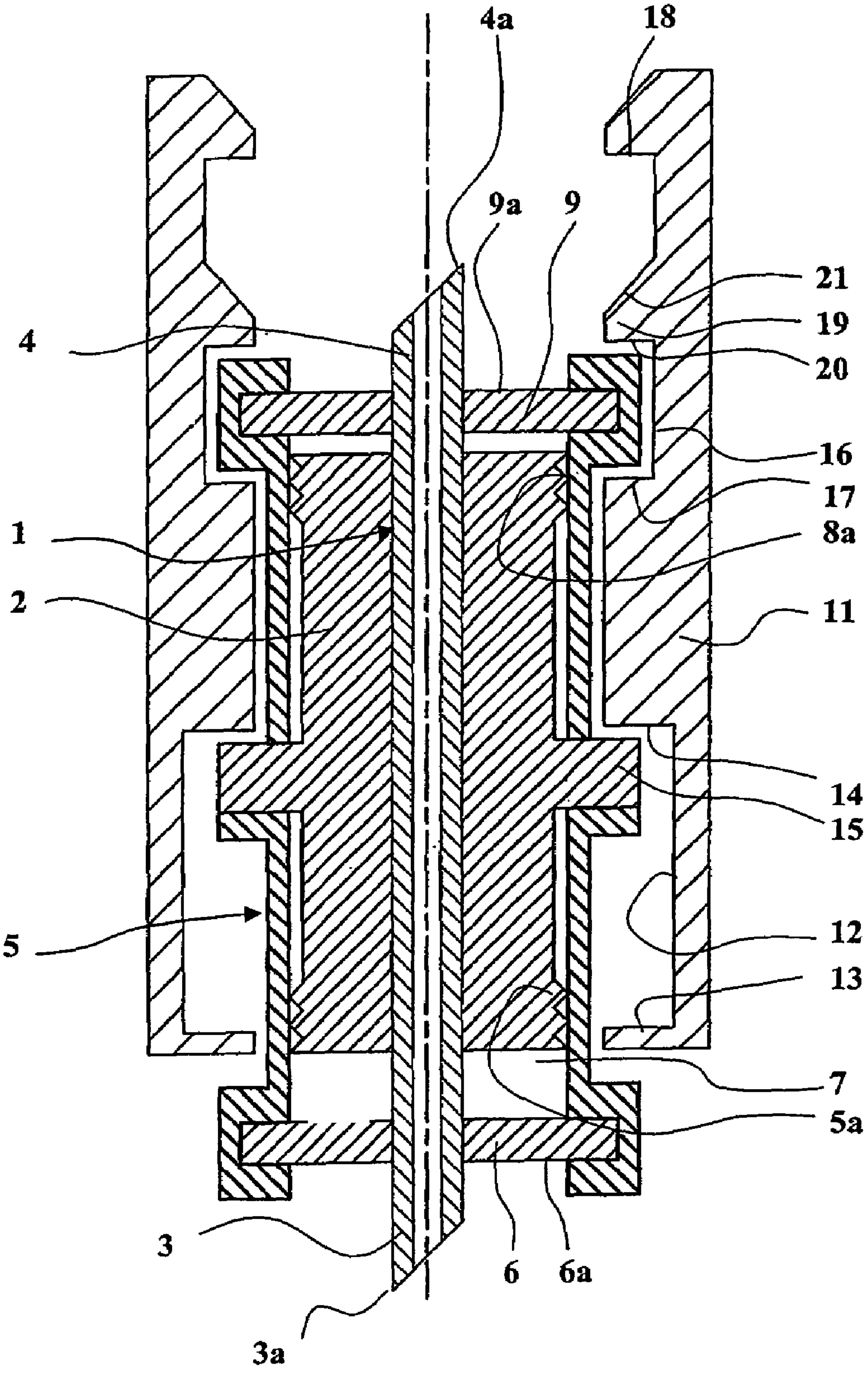
FIG. 4 is a side view in section of the FIG. 1 connection after a second piercing stroke.

The unilateral engagement means then again allow axial movement of the sleeve 11 in the direction of the first foil 6, over a second piercing stroke, from the FIG. 3 position to the FIG. 4 position, during which stroke the sleeve entrains the second foil 9 axially from its initial position toward its final position for piercing by the needle 1.

To allow these various movements, the sleeve 11 comprises a larger diameter first bore 12 in a first end section of the sleeve 11, and delimited by a first shoulder 13 and a second shoulder 14. The body 2 comprises a larger diameter annular rib 15 engaged in the first bore 12 of the sleeve 11 to allow relative axial movement of the sleeve 11 around the body 2 over an appropriate stroke equal to the first piercing stroke C1. In the end of stroke positions, the annular rib 15 abuts against the shoulder 13 or the shoulder 14.

Also in order to allow the above movements, the sleeve 11 comprises a larger diameter second bore 16 in a second end section of the sleeve 11, and delimited by a third shoulder 17 and a fourth shoulder 18.

The second foil 9 remains engaged in the second bore 16 and moves over an appropriate axial stroke equal to the second piercing stroke C2.

The second bore 16 comprises an intermediate annular rib 19 with a sawtooth transverse profile having an non-inclined first face 20 and an inclined second face 21.

As may be seen in the figures, the first tubular receptacle 5, in the form of the first cylinder, slides in the sleeve 11. Similarly, the second tubular receptacle 8, in the form of the second cylinder, slides in the sleeve 11.

In the initial position shown in FIG. 1, the first cylinder projects out of the sleeve 11, so that the first foil 6 has an external first face 6*a* accessible for disinfection. Similarly, in this same initial position, the second cylinder 8 is engaged in the sleeve 11 with the second foil 9 in the vicinity of the second end of the sleeve 11, so that the external face 9*a* of the second foil 9 is also accessible to the user for disinfecting it.

How the perforating connector of the invention is used is explained hereinafter.

To transport it, the connector is in the state shown in FIG. 1: the first tubular receptacle in the form of the cylinder 5 is away from the body 2 and projects out of the sleeve 11, the first end section 3 of the needle 1 being confined in the first cavity 7 and set back from the first foil 6. The second tubular receptacle 8 is engaged in the sleeve 11 in the vicinity of its second end, the second foil 9 being engaged between the fourth shoulder 18 and the intermediate rib 19, and being away from the body 2. The second end section 4 of the needle 1 is then confined in the second cavity 10.

After cleaning the two external surfaces 6*a* and 9*a* of the foils 6 and 9, respectively, the foil or stopper of a first container is engaged against the first foil 6, and the perforating connector is pushed by means of its sleeve 11 against the first flask, i.e. downward in FIG. 1. The sleeve 11, which at this time bears on the annular rib 15 of the body 2 through the shoulder 14, pushes the body 2 and the needle 1 downward, causing the first end section 3 of the needle 1 to pierce the first foil 6 and the foil or stopper of the first container. Note that the shoulder 18 also entrains the second foil 9 over the same stroke, with the same movement as the body 2, so that the needle 1 always remains set back from the second foil 9.

The sleeve 11 then performs a return stroke, as shown in FIG. 3. During this return stroke, the second foil 9, which is held in axial bearing engagement against the foil or stopper of a second container, allows the intermediate rib 19 to move past it, because of the asymmetrical shape of the rib and elastic radial deformation of the rib 19 and/or the foil 9, and engages under the non-inclined face 20 of the intermediate rib 19.

A second, downward axial movement of the sleeve 11 then entrains the second foil 9 downward, while the body 2 remains immobile with its rib 15 bearing against the first tubular receptacle 5, which in turn bears on the first flask. The second foil 9 is then pierced. At the same time, the needle 1 pierces the foil or stopper of the second container, which is bearing against the second foil 9.

Clearly, at no time is the atmosphere inside the needle brought into contact with the external atmosphere, and the connection is made under optimum sterilization conditions. Moreover, the foils are pierced non-simultaneously by successive intentional actions of the user on the sleeve 11, ruling out premature piercing.

The present invention is not limited to the embodiments explicitly described but includes diverse variants and generalizations thereof that fall within the scope of the following claims.

There is claimed:

1. A perforating connector, comprising a hollow fluid passage needle, a needle support body fixed in a sealed manner around an intermediate section of the needle and allowing a first end section and a second end section of the needle to project, a first tubular receptacle around the first end section of the needle and conformed to receive a first element to be connected, a second tubular receptacle around the second end section of the needle and conformed to receive a second element to be connected, a first foil closing the first tubular receptacle, a second foil closing the second tubular receptacle, the first foil being movable axially relative to the needle support body over a first piercing stroke between an initial position away from the body and the needle and a final position close to the body in which the needle passes through the first foil and its end projects toward the exterior of the connector, this second foil being movable axially relative to the needle support body over a second piercing stroke between an initial position away from the body and the needle and a final position close to the body in which the needle passes through the second foil and its end projects toward the exterior of the connector, wherein the perforating connector comprises a coaxial external holding sleeve adapted for moving the body and the second foil axially toward the first foil over the first piercing stroke without piercing the second foil, and then for moving the second foil axially toward the body and toward the first foil over the second piercing stroke.

2. A connector according to claim 1, wherein:

- the sleeve comprises unilateral engagement means to enable the sleeve to push the body and the second foil axially toward the first foil when the sleeve moves axially over a distance equal to the first piercing stroke in the direction of the body, and for the sleeve to be disengaged axially from the body and the second foil when the sleeve effects a return stroke in the opposite direction away from the first foil and over a distance equal to the first piercing stroke,
- the sleeve comprises non-return engagement means, in order for the sleeve to allow the second foil to be retained in a fixed position relative to the body during the return stroke in the opposite direction of the sleeve, and then to entrain the second foil axially from its initial position toward its final position when the sleeve effects a second piercing stroke in the direction of the first foil.

3. A connector according to claim 2, wherein the unilateral engagement means of the sleeve comprise:

a first larger diameter bore on a first end section of the sleeve delimited by a first shoulder and a second shoulder, and a larger diameter annular rib on the body, engaged in the first bore of the sleeve to allow relative axial movement of the sleeve around the body over an appropriate stroke equal to the first piercing stroke between two limiting positions in which the annular rib is abutted against one or the other of the shoulders.

4. A connector according to claim 2, wherein the unilateral engagement means of the sleeve comprise:

a larger diameter second bore in a second end section of the sleeve delimited by a first shoulder and a second shoulder, and the second foil being engaged in the second bore to move over an appropriate axial stroke equal to the second piercing stroke.

5. A connector according to claim 4, wherein the second bore comprises an annular intermediate rib having a saw-tooth transverse profile with a non-inclined first face and an inclined second face, and cooperating with the second foil to allow it to move in the direction of the first foil and to prevent any return movement thereof in the opposite direction.

6. A connector according to claim 1, wherein the first foil is mounted on a first tubular receptacle in the form of a first cylinder that slides in the sleeve and slides on the body with sealed sliding means between them.

7. A connector according to claim 1, wherein the second foil is mounted on a second tubular receptacle in the form of a second cylinder that slides in the sleeve and slides on the body with sealed sliding means between them.

8. A connector according to claim 6, wherein, in an initial position, the first cylinder projects out of the sleeve, and the second cylinder is engaged with the second foil in the vicinity of the second end of the sleeve to leave the external faces of the foils accessible from the outside.

9. A perforating connector, comprising a hollow fluid passage needle, a needle support body fixed in a sealed manner around an intermediate section of the needle and allowing a first end section and a second end section of the needle to project, a first tubular receptacle around the first end section of the needle and conformed to receive a first element to be connected, a second tubular receptacle around the second end section of the needle and conformed to receive a second element to be connected, a first foil closing the first tubular receptacle, a second foil closing the second tubular receptacle, the first foil being movable axially relative to the needle support body over a first piercing stroke between an initial position away from the body and the needle and a final position close to the body in which the needle passes through the first foil and its end projects toward the exterior of the connector, this second foil being movable axially relative to the needle support body over a second piercing stroke between an initial position away from the body and the needle and a final position close to the body in which the needle passes through the second foil and its end projects toward the exterior of the connector, wherein the perforating connector comprises a coaxial external holding sleeve adapted for moving the body and the second foil axially toward the first foil over the first piercing stroke, and then for moving the second foil axially toward the body and toward the first foil over the second piercing stroke, wherein:

the sleeve comprises unilateral engagement means to enable the sleeve to push the body and the second foil axially toward the first foil when the sleeve moves axially over a distance equal to the first piercing stroke in the direction of the body, and for the sleeve to be disengaged axially from the body and the second foil when the sleeve effects a return stroke in the opposite direction away from the first foil and over a distance equal to the first piercing stroke, the sleeve comprises non-return engagement means, in order for the sleeve to allow the second foil to be retained in a fixed position relative to the body during the return stroke in the opposite direction of the sleeve, and then to entrain the second foil axially from its initial position toward its final position when the sleeve effects a second piercing stroke in the direction of the first foil.

10. A connector according to claim 9, wherein the unilateral engagement means of the sleeve comprise:

a first larger diameter bore on a first end section of the sleeve delimited by a first shoulder and a second shoulder, and a larger diameter annular rib on the body, engaged in the first bore of the sleeve to allow relative axial movement of the sleeve around the body over an appropriate stroke equal to the first piercing stroke between two limiting positions in which the annular rib is abutted against one or the other of the shoulders.

11. A connector according to claim 9, wherein the unilateral engagement means of the sleeve comprise:

a larger diameter second bore in a second end section of the sleeve delimited by a first shoulder and a second shoulder, and the second foil being engaged in the second bore to move over an appropriate axial stroke equal to the second piercing stroke.

12. A connector according to claim 11, wherein the second bore comprises an annular intermediate rib having a saw-tooth transverse profile with a non-inclined first face and an inclined second face, and cooperating with the second foil to allow it to move in the direction of the first foil and to prevent any return movement thereof in the opposite direction.

* * * * *